United States Patent [19]

Dieringer

[11] Patent Number: 5,297,776
[45] Date of Patent: Mar. 29, 1994

[54] COUPLING DEVICE FOR THE CONNECTION OF TUBE LINES USED FOR MEDICAL PURPOSES

[76] Inventor: Franz A. Dieringer, Prinz Eugenstrasse 18/II/18, A-1040 Vienna, Austria

[21] Appl. No.: 930,437
[22] PCT Filed: Jan. 22, 1992
[86] PCT No.: PCT/AT92/00007
  § 371 Date: Sep. 22, 1992
  § 102(e) Date: Sep. 22, 1992
[87] PCT Pub. No.: WO92/12760
  PCT Pub. Date: Aug. 6, 1992

[30] Foreign Application Priority Data

Jan. 22, 1991 [AT] Austria .................... 135/91

[51] Int. Cl.⁵ ............................................ A61M 39/00
[52] U.S. Cl. ............................. 251/149.1; 604/249
[58] Field of Search ............ 251/149.1, 149.8, 149.9; 604/256, 247, 236, 249, 246, 33, 91

[56] References Cited

U.S. PATENT DOCUMENTS

| | | | |
|---|---|---|---|
| 3,409,015 | 11/1968 | Swanson | 251/149.1 X |
| 3,896,853 | 7/1975 | Bernhard | 604/249 X |
| 4,710,168 | 12/1987 | Schwab et al. | 251/149.1 X |
| 5,034,000 | 7/1991 | Freitas et al. | 604/33 X |
| 5,049,128 | 9/1991 | Duquette | 604/249 X |

FOREIGN PATENT DOCUMENTS

| | | |
|---|---|---|
| 386523 | 12/1988 | Austria . |
| 0116986 | 8/1984 | European Pat. Off. . |
| 0198407 | 10/1986 | European Pat. Off. . |
| WO90/07953 | 7/1990 | World Int. Prop. O. . |

*Primary Examiner*—Martin P. Schwadron
*Assistant Examiner*—Kevin L. Lee
*Attorney, Agent, or Firm*—Jacobson, Price, Holman & Stern

[57] ABSTRACT

In a coupling device for the connection of tubes for medical purposes, a first coupling-part (1) within which is mounted an axially adjustable hollow pin (2) provided with radial inlet openings (19) for the attachment of an initial tube piece, which pin (2) when in an operating position runs through an absorbent insert (9) impregnated with disinfectant and opens by way of its radial inlet openings (19) into a second coupling part (5) connected in detachable fashion to the first coupling part (1), while the second coupling part (5) exhibits at least an attachment point (7) and a vent (8), the second coupling part (5) exhibits a longitudinally adjustable sealing component (11) for a centrally positioned vent (8), while the hollow pin (2) exhibits an extension (29) serving the adjustment of the sealing component (11).

18 Claims, 2 Drawing Sheets

COUPLING DEVICE FOR THE CONNECTION OF TUBE LINES USED FOR MEDICAL PURPOSES

BACKGROUND OF THE INVENTION

The invention relates to a coupling device for connecting tube lines used in medicine, with an initial coupling part within which is mounted an axially adjustable hollow pin exhibiting outlet openings and serving to attach an initial coupling part which in operating position runs through a sponge that can be impregnated with disinfectant and which opens by way of its outlet openings into a second coupling part connected in detachable form to the first coupling part, while the second coupling part exhibits at least two attachment openings.

A device of this type is known to the prior art from WO 90/07953. In the known procedure of sterilely connecting tube lines for medical purposes, a hollow pin is held in axially adjustable position in a coupling part, while with the axial adjustment of the pin the free end, facing away from the tube-connecting end of the pin, moves through elastically deformable inserts, which can be impregnated with disinfectant, into the second coupling part. This second coupling part which can be connected to the first coupling part exhibits two openings: a central vent, which is closed by an extension of the pin when the latter is moved into its terminal position, and a second opening of the second coupling part, which can be used to connect infusion bottles, bags, and the like, directly to the patient. In devices like that of WO 90/07953 the replacement of such infusion bottles, bags, and the like, required only that the pin again be moved through the lip seal and through the wiping areas to its initial position in order to assure that there was a tight seal for the infusion solution during replacement of the infusion equipment or the like, to thereby reduce the danger of infection. After changing the infusion bottles, bags, etc., the hollow pin could again be moved into its adjusted position and infusion solutions, or the like, again be fed to the patient by producing an open connection between the infusion bottle and the hollow pin. In order to seal the vent when adjusting the pin it was necessary in the known design to press the hollow pin and its extension into the vent under high mechanical pressure.

SUMMARY OF THE INVENTION

The goal of the invention is to create a device of the type described above in which contamination of the infusion solution by disinfectants, ambient air, or the like is avoided with certainty and a vent or additional attachment opening can be tightly sealed with a low mechanical load on the hollow pin. To solve this problem the invention basically consists in the fact that the second coupling part exhibits a sealing component adjustable in the longitudinal direction for a centrally positioned connecting hole and the hollow pin exhibits a stop face for the adjustable sealing component. The fact that the second coupling part displays a longitudinally adjustable sealing component for a centrally placed attachment opening assures that in the axial adjustment of the hollow pin the centrally positioned attachment opening is securely sealed by the adjustable sealing component and the hollow pin is not exposed to any unduly high mechanical loads that might arise in adjusting and turning the pin in the centrally positioned attachment hole. Because the hollow pin exhibits a contact surface or stop face for the adjustment of the sealing component, the sealing component can be moved axially merely by positioning the hollow pin on its side turned away from the centrally positioned attachment hole, while such adjustment again exposes the hollow pin to extremely low mechanical loads.

The second coupling part is advantageously designed in such a way that the sealing component is guided in non-rotating fashion in the longitudinal direction of the coupling device. Because the sealing component is guided in non-rotating fashion in the longitudinal direction of the coupling device it is assured that when moved in the longitudinal direction the sealing component cannot tilt or become wedged in an undesirable fashion and thereby impair the complete closure of the centrally positioned attachment opening. With the non-rotating positioning of the sealing component in the longitudinal direction of the coupling device a secure closure of the centrally positioned attachment opening is assured with no essential expenditure of force and without a large mechanical load being placed on either the sealing component or the hollow pin. The non-rotating positioning of the sealing component in the longitudinal direction of the coupling is assured with particular advantage in that the sealing component exhibits at least one basically radial extension which engages with a longitudinal recess or groove in the inner jacket of the second coupling part. This engaging of the basically radial extension in a longitudinal recess or groove in the inner jacket of the second coupling part creates a guide for moving the sealing component in the axial direction and also guarantees a sure sealing of the centrally positioned attachment opening in the second coupling part. In order to guarantee not only a sure sealing of the centrally positioned attachment opening but also a tight sealing of this attachment opening, the invention is further elaborated to advantage in that the sealing component exhibits an extension, specifically a conical extension, which interacts with the centrally positioned attachment opening, specifically of hollow-conical design, while in a particularly preferred embodiment the attachment opening interacting with the extension supports a sealing element on its inner circumference. Because the sealing component exhibits a conical extension interacting with the corresponding hollow-conical attachment opening which supports a sealing element on its inner circumference, the centering action intended to achieve a tight sealing for the centrally positioned attachment opening is assured with a simultaneous low mechanical load, while the tight sealing of the centrally positioned attachment opening prevents with certainty the penetration of substances contaminating the infusion solutions, for example, foreign particles or ambient air.

The second coupling part is designed to particular advantage in that the attachment opening that interacts with the extension exhibits at least one locking element, specifically, teeth-like projections which interact with corresponding locking elements in the sealing component. Due to the attachment opening that interacts with the extension exhibiting a locking element that interacts with corresponding locking elements in the sealing component, a tight and inseparable connection is created between the sealing component and the centrally positioned attachment opening. Such an inseparable connection between the sealing component and the centrally positioned attachment opening assures that after closing the centrally positioned attachment opening the sealing element cannot be reopened and thus that the second coupling part can only be used a single time. Preventing the reuse of the second coupling part thus reduces the risk of contaminating substances being drawn into the coupling device through the centrally positioned attachment opening when the pin is retracted and the containers for infusion liquids are changed, and thus guarantees that absolutely sterile conditions are maintained in the coupling during the feed of infusion solutions.

In order to guarantee the simple and safe adjustment of the sealing component by means of the hollow pin in the inner part of the second coupling part, the device according to the invention is basically designed so that on its side facing away from the attachment opening the sealing component exhibits a recess or extension which interacts with an extension or recess in the hollow pin. Inasmuch as the sealing component exhibits on its side facing away from the attachment opening a recess or an extension that interacts with an extension or recess in the hollow pin, wedging or tilting of the hollow pin during axial adjustment along the coupling device is avoided with certainty and a precisely facing placement of the movable elements is maintained.

The second coupling part is advantageously designed such that the sealing component in OPEN position is mounted in sealed fashion at a distance from the attachment opening, while the mounting advantageously exhibits a circular sealing with inlet holes. With the sealed mounting of the sealing component while in OPEN position, the space formed in the upper part of the second coupling part is sealed against the side facing away from the attachment openings and the space located in the upper part of the second coupling part can be filled with infusion solution, or other pharmaceutical agents fed to the patient, without the incorporation of air bubbles before the sealing component is moved into CLOSED position. By fitting the outer diameter of the hollow pin to that of the sealing component, the sealed position of the pin in operating position is also assured.

The coupling device according to the invention is advantageously designed such that the hollow pin, in its position corresponding to the sealing component's closed position, is guided in turning fashion by a slotted link employing a radial actuating member running through the wall of the first coupling part, while the slotted link rests on a plane that is inclined relative to the normal plane along the pin axis. Since the hollow pin is guided in turning fashion by a slotted link by means of an actuating member running through the wall of the first coupling part, after the pin has been positioned and turned in the slotted link it is impossible for it to slide back into its initial position. Since the slotted link rests on a plane that is inclined relative to the normal plane along the pin axis, the extension or recess of the hollow pin is assured a secure fit in the sealing component and thus a secure fit of the sealing component extension in the centrally positioned attachment opening of the second coupling part is also assured, and the OPEN position of the entire coupling device is established.

The invention will next be described on the basis of an embodiment example shown in the drawing.

BRIEF DESCRIPTION OF A PREFERRED EMBODIMENT

Figure 1:
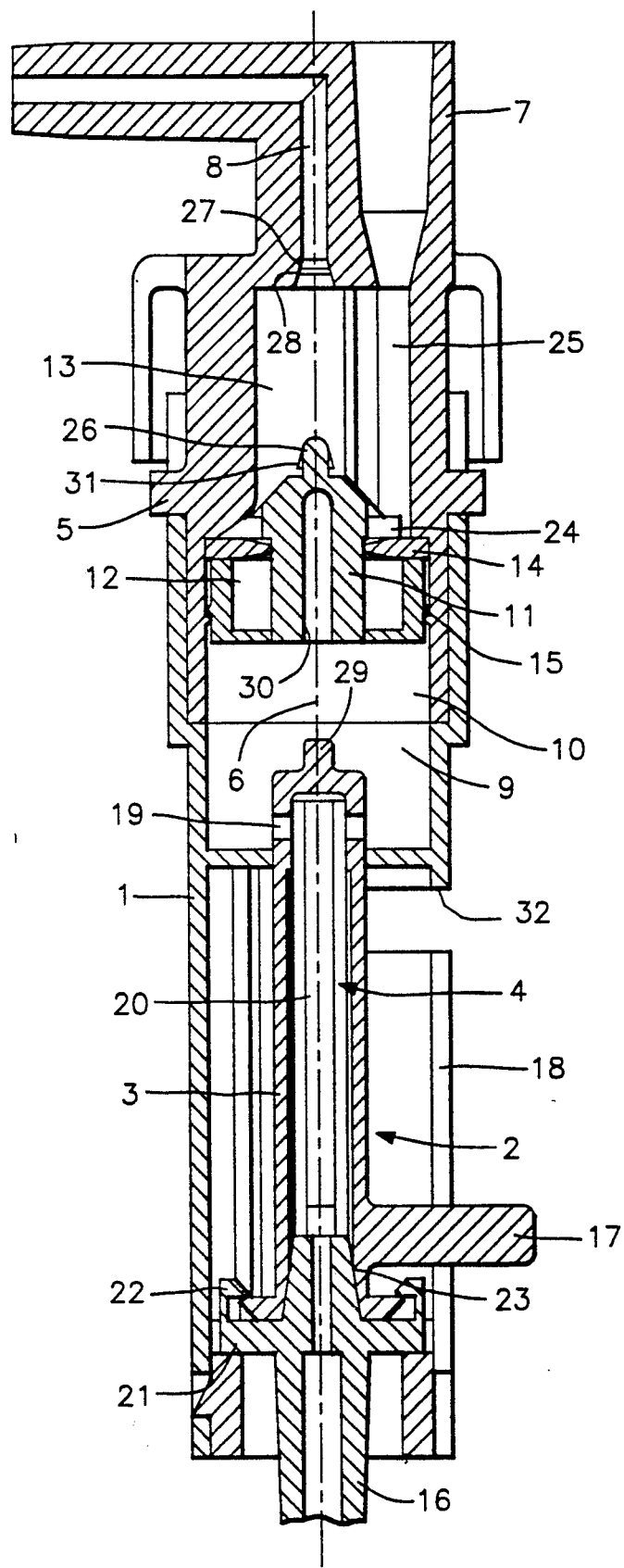
FIG. 1 shows a schematic depiction of the invention coupling device in axial section in a NON-OPERATING position and FIG. 2 shows a comparable depiction with the hollow pin in an OPERATING position.

FIG. 1 shows an initial coupling part 1 with a pin 2 that slides in the axial direction, the pin 2 consisting of an outer part 3 and an inner part 4. Attached to the first coupling part 1 is a second coupling part 5 in which an attachment point 7 is provided, eccentric to the axis 6 of the pin or of the sliding path of the pin, for a tube line continuing on to infusion equipment. A vent 8 is provided on the second coupling part 5 central to and within the axis 6. When the pin 2 is moved axially, the pin 2 is first moved through an initial insert 9 of absorbent material, which is permanently impregnated with disinfectant. A second, axially adjacent insert 10, which can be replaceable if so desired, is contained in the second coupling part to supplement the disinfectant and assure a high degree of disinfection. Provided in the second coupling part 5 are a sealing component 11 for the vent 8, which sealing component 11 moves in the longitudinal direction of the coupling part 5, and an absorbent wiping insert 12, which wipes off and absorbs any matter sticking to the outside of the pin 2.

When an infusion bottle is attached to the attachment point 7, de-aeration is provided by feeding the incoming medium into the space 13 until it flows out of the vent 8. In order to assure that during this rinsing process for the removal of residual air the wiping insert 12 does not come into contact with the medium—and thus is not impregnated with the medium and does not lose its absorptive capacity—the sealing component 11 is held in a circular seal 14. The wiping insert 12 and the circular seal 14 are held together in a common structural component 15 which engages with the second coupling part 5.

To assure that when the pin is in withdrawn position, as shown in a FIG. 1, the line leading to the patient and attached to the pin at a connecting element point 16 is properly sealed at said connecting element 16, the outer part 3 of the pin is equipped with a radial actuating extension 17, which runs through a guide channel in the wall of the first coupling part 1. The inner pin part 4 is in contact with the connecting element 16, while in the turning position shown in FIG. 1, the inner pin part 4 is seized and sealed by the outer part 3 of the pin, so that in the position shown in FIG. 1 a set of radial openings 19 in the outer part 3 of the pin remain sealed.

The inner pin 4 exhibits channels running in the axial direction which in the predetermined turning position can be brought flush with the radial openings 19 in the outer part 3 of the pin. The inner part 4 of the pin is connected to a base part 21, which is furnished with dogs 32 for locking the outer part 3 of the pin 2. The connecting element 16 of the line leading to the patient opens from the base part 21 into the space running in axial direction, which is bordered by the recesses 20 of the inner part of the pin 4 and the inner wall of the outer part 3 of the pin. The base part also exhibits a conical sealing area 23 which forms a sealing area for the outer part 3 of the pin after insertion of the outer part of the pin in a snap-in position which is secured against axial displacement by the dogs 22 of the base part.

In the NON-OPERATING position shown in FIG. 1, the separate sealing component 11 which can be moved in the axial direction of the coupling device is held in the sleeve-like component by the circular seal 14 and is guided in a non-turning fashion within the second coupling part 5. To this end the sealing component 11 exhibits a basically radial extension 24, which interacts with a recess or groove 25 running basically in the axial direction on the inner surface of the second coupling part, while the groove in the depicted embodiment aligns with attachment point 7 and an infusion bottle, which is not depicted. The sealing component 11 also exhibits a conical extension 26, which fits into the vent 8 or in the centrally positioned opening when the sealing component 11 is moved, while the vent 8 exhibits a conical area 27 fitted to the conical shape of the extension and supports a sealing 28 to improve the seal effect. In order to permit the proper interaction of the hollow pin 2 with the sealing component 11 when the pin 2 is moved, at its end facing the sealing component 11 the hollow pin 2 exhibits a stop fare in the form of an extension 29, which extension 29 fits with a correspondingly shaped recess or opening 30 in the sealing component 11. This supports the straight alignment of the sealing component 11 in the second coupling part when the pin 2 is moved forward. To prevent the repeated use of the second coupling port after the infusion containers have been replaced, the conical extension 26 can be provided with, e.g., locking elements 31 which engage with corresponding recesses (not shown) in the vent 8 upon the initial insertion of the axial pin as depicted in FIG. 2 and such that the sealing component 11 remains in the position shown in FIG. 2 when the pin 2 is retracted and further use will call for at least the replacement of the second coupling part.

To prevent infusion solutions or medications located in space 13 from penetrating into the area of the absorbent inserts 9, 10, or 12 impregnated with disinfectant or serving to wipe said area when the pin is in an inserted position, the outer diameter of the outer part 3 of the pin can be slightly larger than the outer diameter of the area of the sealing component 11 facing away from the extension 26, to thereby maintain the sealing effect of the circular seal 14.

Figure 2:
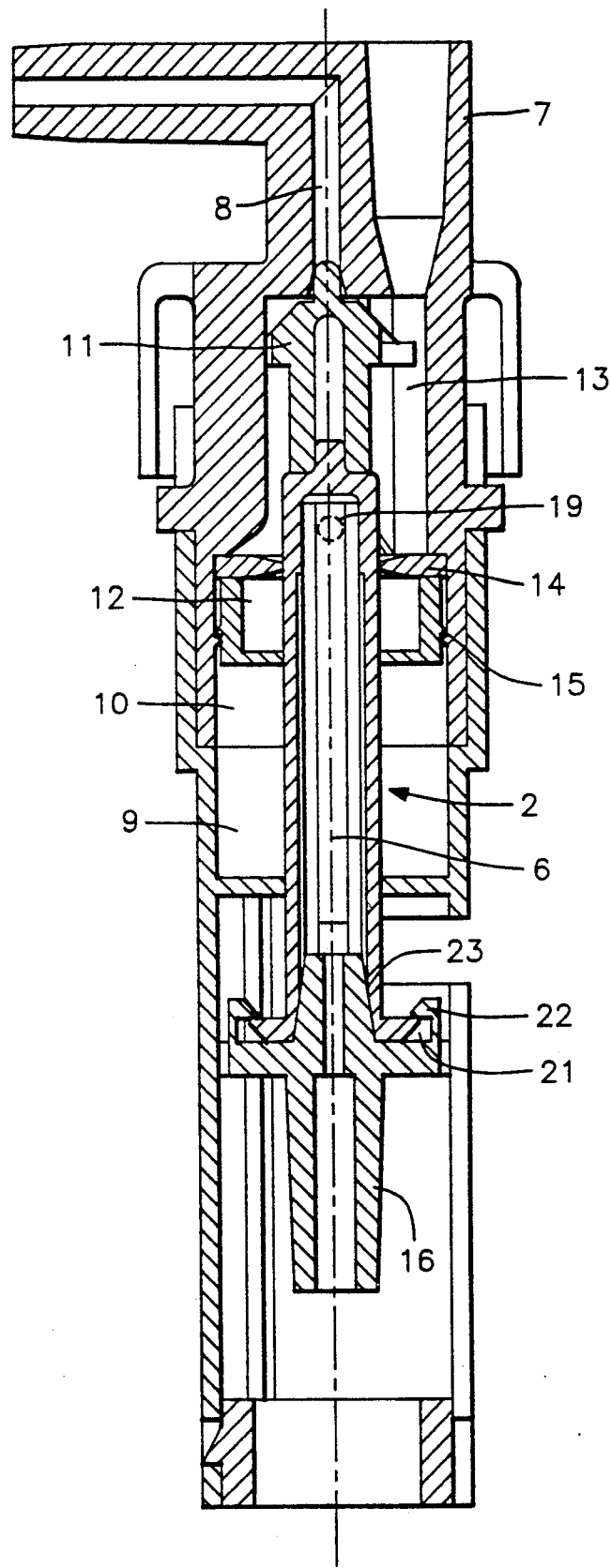

As indicated above, the axial pin 2 is actuated by means of a radial actuating extension 17, which moves in the axial direction of the coupling device within an initial partial area 18 of a slotted link, while adjoining this initial partial area 18 is a partial area 32 of the slotted link arrangement that runs basically normal to said partial area 18; when the outer part 3 of the hollow pin 2 is turned by actuating the lever 17, the radial openings 19 reach the position indicated by the broken line in FIG. 2, thereby creating a connection between the space 13 and the axially running channels or recesses 20 in the inner part 4 of the pin. To permit a precise fit of the sealing component 11 in the vent 8, the partial area 32 of the slotted-link arrangement runs on a plane that is inclined relative to the normal plane of the axis 6 of the pin 2; here the incline runs in the direction of the second coupling part, so that turning the pin results in a further slight axial motion in the direction of the second coupling part and the sealing component 11 is pressed into the vents.

The centrally located opening 8 can be used not only for de-aeration but also to feed additional medications into the space 13 and then to the patient.

I claim:

1. Coupling device for the connection of tubes for medical purposes, with a first coupling part for the attachment of an initial tube piece, said first coupling part having mounted therein an axially adjustable hollow pin provided with inlet openings, which hollow pin when in an operating position runs through an absorbent insert impregnated with disinfectant and opens by way of its inlet openings into a second coupling part connected in detachable fashion to the first coupling part, while the second coupling part includes at least an attachment opening and a vent; wherein the second coupling part includes a longitudinally adjustable sealing component for the vent, said vent being centrally positioned; wherein the hollow pin includes a stop face for providing straight alignment of the sealing component; and wherein the sealing component includes a conical extension which interacts with the centrally positioned vent, said vent having a hollow-conical portion.

2. Coupling device of claim 1, wherein the sealing component runs in non-rotating fashion in the longitudinal direction of the coupling device.

3. Coupling device of claim 1, wherein the sealing component includes at least one substantially radial extension which engages a longitudinal recess or groove formed inside the second coupling part.

4. Coupling device of claim 1, wherein the hollow conical portion of the vent supports a seal.

5. Coupling device of claim 1, wherein the sealing component includes on a side opposite from the vent a recess, and wherein said stop face comprises a first extension which interacts with said recess on the side of the sealing component opposite from the vent.

6. Coupling device of claim 1, wherein the sealing component in the OPEN position is mounted in a sealed fashion and is spaced apart from the vent of the second coupling part.

7. Coupling device of claim 1, wherein the vent includes an inlet having a ring seal mounted therein.

8. Coupling device of claim 1, wherein the hollow pin, in its adjustment position corresponding to the closed position of the sealing component, is guided for rotation about a longitudinal axis thereof, said hollow pin being guided in a slotted link by means of a radial actuating member that extends through the first coupling part, and wherein said slotted link lies on a plane that is inclined relative to a normal plane on the longitudinal axis of the hollow pin.

9. Coupling device of claim 1, wherein the sealing component includes on a side opposite from the vent a first extension, and wherein said stop face comprises a recess which engages said first extension.

10. Coupling device for the connection of tubes for medical purposes, with a first coupling part for the attachment of an initial tube piece, said first coupling part having mounted therein an axially adjustable hollow pin provided with inlet openings, which hollow pin when in an operating position runs through an absorbent insert impregnated with disinfectant and opens by way of its inlet openings into a second coupling part connected in detachable fashion to the first coupling part, while the second coupling part includes at least an attachment opening and a vent; wherein the second coupling part includes a longitudinally adjustable sealing component for the vent, said vent being centrally positioned; wherein the hollow pin includes a stop face for providing straight alignment of the sealing component; and wherein the vent includes at least one locking element comprising tooth-like projections which interact with corresponding locking elements in the sealing component.

11. Coupling device of claim 10, wherein the sealing component runs in non-rotating fashion in the longitudinal direction of the coupling device.

12. Coupling device of claim 10, wherein the sealing component includes at least one substantially radial extension which engages a longitudinal recess or groove formed inside the second coupling part.

13. Coupling device of claim 10, wherein the vent supports a seal.

14. Coupling device of claim 10, wherein the sealing component includes on a side opposite from the vent a recess, and wherein said stop face comprises a first extension which interacts with said recess on the side of the sealing component opposite from the vent.

15. Coupling device of claim 10, wherein the sealing component in the OPEN position is mounted in a sealed fashion and is spaced apart from the vent of the second coupling part.

16. Coupling device of claim 10, wherein the vent includes an inlet having a ring seal mounted therein.

17. Coupling device of claim 10, wherein the hollow pin, in its adjustment position corresponding to the closed position of the sealing component, is guided for rotation about a longitudinal axis thereof, said hollow pin being guided in a slotted link by means of a radial actuating member that extends through the first coupling part, and wherein said slotted link lies on a plane that is inclined relative to a normal plane on the longitudinal axis of the hollow pin.

18. Coupling device of claim 10, wherein the sealing component includes on a side opposite from the vent a first extension, and wherein said stop face comprises a recess which engages said first extension.

* * * * *